US008606363B2

(12) United States Patent
Suaning et al.

(10) Patent No.: US 8,606,363 B2
(45) Date of Patent: Dec. 10, 2013

(54) ELECTRODE MULTIPLEXING METHOD FOR RETINAL PROSTHESIS

(75) Inventors: Gregg Jorgen Suaning, Narara (AU); Nigel Hamilton Lovell, Coogee (AU)

(73) Assignee: Newsouth Innovations Pty Limited, New South Wales (AU)

( * ) Notice: Subject to any disclaimer, the term of this patent is extended or adjusted under 35 U.S.C. 154(b) by 756 days.

(21) Appl. No.: 12/275,094

(22) Filed: Nov. 20, 2008

(65) Prior Publication Data

US 2009/0287275 A1    Nov. 19, 2009

Related U.S. Application Data

(63) Continuation of application No. 11/112,571, filed on Apr. 25, 2005, now abandoned.

(60) Provisional application No. 60/564,476, filed on Apr. 22, 2004.

(51) Int. Cl.
*A61N 1/372* (2006.01)

(52) U.S. Cl.
USPC ............................................. 607/54; 607/55

(58) Field of Classification Search
USPC ......................................... 607/53–54, 55–57
See application file for complete search history.

(56) References Cited

U.S. PATENT DOCUMENTS

| | | | |
|---|---|---|---|
| 4,532,930 A | | 8/1985 | Crosby et al. |
| 4,628,933 A * | | 12/1986 | Michelson ....................... 607/53 |
| 5,109,844 A * | | 5/1992 | de Juan et al. .................. 607/53 |
| 5,556,423 A | | 9/1996 | Chow et al. |
| 6,195,585 B1 * | | 2/2001 | Karunasiri et al. ............. 607/57 |
| 6,393,327 B1 | | 5/2002 | Scribner |
| 6,458,157 B1 * | | 10/2002 | Suaning ....................... 623/6.63 |
| 7,079,900 B2 * | | 7/2006 | Greenburg et al. ............. 607/54 |
| 7,338,522 B2 * | | 3/2008 | Greenberg et al. ........... 623/6.63 |
| 7,840,273 B2 * | | 11/2010 | Schmid ........................... 607/53 |
| 8,428,740 B2 * | | 4/2013 | Gefen et al. .................... 607/54 |

OTHER PUBLICATIONS

Al Marshad, H.A., Lee, K. F., and Enderle, J.D., Induced Pain Inhibiting System (IPIS): New Technique to Manipulate Experimental Pain in Human Subject by Using Electrical Stimulation with Hexagonal Electrodes Ring Set, Proceedings of the IEEE 27th Annual Northeast Bioengineering Conference, 2001.

Brindley, G.S. et al., The sensations produced by electrical stimulation of the visual cortex, J Physiol, 1968, 196(2): 479-93.

Cha, K. et al., Simulation of a Phosphene-based visual field: visual acuity in a pixelized vision system, Annals of Biomedical Engineering, 1992, 20: 439-449.

(Continued)

*Primary Examiner* — Carl H Layno
*Assistant Examiner* — Luther Behringer
(74) *Attorney, Agent, or Firm* — Knobbe, Martens, Olson & Bear, LLP

(57) ABSTRACT

A method is disclosed for efficient multiplexing of a plurality of electrodes in a nerve stimulator using improved, predetermined, regular, repeatable geometric patterns arranged in a predetermined mosaic to form a desired array. Multiple electrodes within said array are addressed by the nerve stimulator as being a stimulating electrode by an instruction specifying a single identifier, indicating a position within each regular geometric pattern. As such, each electrode within the array, maintaining the specified position within its respective repeatable geometric pattern, becomes a stimulating electrode and is connected to the appropriate electronic circuit for subsequent, potential use in nerve stimulation.

43 Claims, 13 Drawing Sheets

(56) References Cited

OTHER PUBLICATIONS

Greenberg, R. J. et al., A computational model of electrical stimulation of the retinal ganglion cell, IEEE Trans. Biomed. Eng., 1999, 46: 505-514.

Huang, CQ, et al., Direct Current Measurements in Cochlear Implants, An in-vivo and in-vitro Study, IEEE 2nd International Conference on Bioelectromagnetism, 1998, Melbourne, Australia.

Humayun, H.S., et al., Visual perception elicited by electrical stimulation of retina in blind humans, Arch Ophthalmol, 1996, 114(1): 40-6.

Humayun, M.S., et al., Pattern electrical stimulation of the human retina, Vis. Res., 1999, 39(15): 2569-2576.

Marg, E. et al., Reported visual percepts from stimulation of the human brain with microelectrodes during therapeutic surgery, Confinia Neurologica, 1965, 26 (2): 57-75.

Nashold Jr., B.S., Phosphenes resulting from stimulation of the midbrain in man, Arch Ophthalmol, 1970, 84(4): 433-6.

Rattay, F. et al., Mechanisms of electrical stimulation with neural prosthesis, Neuromodulation, 2003, 6: 42-56.

Roth, B., The electrical properties of tissues, In: The Biomedical Engineering Handbook, Bronzino, J. D. Ced.), CRC Press, Florida, 1995, pp. 126-138.

Scribner, D., et al., Intraocular retinal prosthesis test device, Proceedings of the 23rd Annual International Conference of the IEEE/Engineering in Medicine and Biology Society, Oct. 25-28, 2001, pp. 3430-3435.

Shandurina, A.M. et al., Evoked potentials to contact electrical stimulation of the optic nerves, Hum Physiol, 1986, 12(I): 9-16.

Suaning, G.J. et al., An efficient multiplexing method for addressing large numbers of electrodes in a visual neuroprosthesis, Proc. $26^{th}$ Annual International Conference of the IEEE EMBS, Sep. 1-6, 2004, San Francisco, CA, 4 pages.

Veraart, C. et al., Pattern Recognition with the Optic Nerve Visual Prosthesis, Artificial Organs, 2003, 27 (11): 996-1004.

\* cited by examiner

Fig. 2 *Prior Art*

ELECTRODE MULTIPLEXING METHOD FOR RETINAL PROSTHESIS

CROSS REFERENCE TO DISCLOSURE DOCUMENTS

This application is based upon Provisional Application for Patent 60/564,476 filed Apr. 22, 2004. Priority is claimed thereto.

FIELD OF THE INVENTION

The present invention is directed generally to approaches to electronic neuroprostheses. More specifically, the present invention is directed to the use of improved multiplexing of stimulation signals to arrays for retinal prostheses using electrode array configurations and switching logic.

BACKGROUND OF THE INVENTION

A single electrode has proven to elicit the perception of a spot of light, a so-called phosphene, in humans with vision impairment. U.S. Provisional Application 60/473,304, filed May 29, 2003 disclosed the implantation of electronic devices wholly or partially at the retina, with an array of electrodes provided to deliver electrical stimulation to remaining intact retinal neurons. An improved arrangement of electrodes was disclosed comprising a stimulation array whereby electrodes are arrayed, in whole or in part, in a staggered pattern allowing for a high density of phosphenes, but wherein the elicitation of discrete phosphene is nonetheless achievable. (See FIG. 1)

In such an array each electrode of said stimulation array is relatively large by comparison to remaining intact retinal neurons, stimulating many neurons when actuated. In such an array, an electrode primarily activates intact retinal neurons that lie on the small, retinal region directly adjacent to the center of said electrode. With increased stimulation, said region of activation increases, a phenomenon approximately modeled by circular regions of increasing radii, concentric to said adjacent region.

For an electronic retinal prosthesis, electrodes effectively render an image by way of phosphenes in the implant recipient's visual field. This is achieved by way of each electrode activating a population of retinal neurons in a discrete region; each population pertaining to the perception of a phosphene. A high density of rendered phosphenes (and therefore a high density of electrodes) is desirable for it allows better visual acuity in the implant recipient. This density, however, is constrained by interference. If any two regions of activation are too close, injected charge will interfere, meaning that the elicitation of discrete phosphenes can not be achieved. For example, an intraocular array of two, small, stimulating electrodes which, when actuated maximally, can activate two large, circular regions of retinal tissue. The two stimulating electrodes need be disparate enough such that the two, said circular regions do not interfere. However, since high density is desirable, the two electrodes should be close enough such that the two circular regions meet tangentially.

In light of the above, the problem as to how to array said stimulating electrodes is analogous to the geometric problem regarding optimally packing equi-sized circles on an unbounded plane. It is a geometric result that the densest packing of equi-sized circles on an unbounded plane is a mosaic exhibiting staggering between successive rows and columns, as illustrated by the four rows and seven columns in FIG. 1. An example of this mosaic is the hexagon.

A stimulating prosthesis of non-trivial complexity must be configured to deliver electrical stimuli. Typically this is achieved by way of switching, via a multiplexing circuit, current or voltage sources to the intended electrodes. Configuring said multiplexing circuit requires instructions to configure, time to convey, and time to act upon said instructions. It is therefore advantageous to reduce either or both the instructions necessary to configure the multiplexing circuit, or the time required for said instructions to be delivered and acted upon.

Utilizing the hexagonal mosaic for electrode layout, or abstracts thereof, a novel multiplexing method for configuring and delivering the stimulus or stimuli from said electrode layout is described.

SUMMARY OF THE INVENTION

In one embodiment, the present invention proposes that stimulating electrodes be arrayed in geometric correspondence, in whole or in part, with a pre-determined staggered pattern and multiplexed according to instructions to appropriate current or voltage sources wherein said instructions are minimised by way of using the electrode geometry to interpret said instructions. One useful pattern having optimal packing density is a dimensionally staggered hexagonal array. Multiplexing of said hexagonal array is achieved by way of an addressing method based upon the hexagaon layout.

An object of this invention is to provide a method for connecting stimulating electrodes to current or voltage sources in a nerve stimulating prosthesis.

It is a further object of this invention to provide such a method for connecting stimulating electrodes to current or voltage sources utilizing the geometric shape of the hexagon as a fundamental means of addressing said stimulating electrodes.

DESCRIPTION OF PRIOR ART

Implantable neural prostheses in mainstream treatment of disease began with the cardiac pacemaker in the 1950s. It is now possible to treat cardiac arrhythmia with pacemakers so that the recipient may lead a near normal life and maintain near normal life expectancy. Later, based upon similar technology, the cochlear implant gave rise to the ability to restore hearing to the deaf and severely hearing impaired. Neural deafness can be treated with cochlear implants to such an extent that a large proportion of recipient patients are able to converse over the telephone, attend mainstream schools and function within society with undetectable disability. Variants of the same technology have been used to restore movement and body function in paralyzed people, and to attenuate tremor in the neurologically diseased.

It may someday be possible to restore useful vision and physical movement to the blind and paralyzed respectively through analogous methods. The division between the two groups described above, those that are commonplace treatments and those that remain in fledgling research, exists as a result of several factors but one of the principal reasons for the substantial successes of the cardiac pacemaker and the cochlear implant is their ability to deliver appropriate electrical stimulation to the appropriate site at the appropriate frequency without exacerbating damage to tissue or the disease condition. For this to occur, an effective means of injecting current and subsequently recovering or safely dissipating this current is required.

The cardiac pacemaker requires only a single stimulation channel (electrode) with the return path for the neurostimulation via the pacemaker capsule itself. For the cochlear implant, substantial benefit can be achieved with as few as 16 stimulation channels and associated electrodes.

In contrast, little visual information can be conveyed with any number of stimulation channels fewer than 64 [Cha 1992], with hundreds or thousands of electrodes necessary to approximate the rich sense of vision that sighted people enjoy. To place this in terms of information flow, the optic nerve of a healthy eye carries approximately one million individual fibres, each of which may transmit chemical signals of an on/off (digital) nature at a rate of up to 200 'bits' per second. This equates to approximately 200 Megabits per second per eye.

The order of stimulation frequency for each of the above examples differ markedly. Assuming a single source of stimuli, said source must supply approximately two stimulus pulses per second for the cardiac pacemaker so as to maintain a heart rate of 120 beats per minute, and up to approximately 15,000 pulses per second for the cochlear implant in order to take advantage of the most modern speech processing techniques [Huang 1998].

In the case of a visual prosthesis, the optimal stimulation rate is not yet established and is likely to be the topic of intense debate well into the future. The practical lower limit of the stimulation rate is the so-called critical flicker fusion (CFF) frequency, below which spots of light (phosphenes) conveyed by way of a visual prosthesis appear pulsatile. The CFF is further dependent upon the site of stimulation, e.g. the retina, optic nerve, lateral geniculate nucleus or visual cortex. It is likely that frequency modulation above the CFF will play a substantial role conveying safe and effective phosphene information in image processing and stimulation strategies. In anticipation of such implementation of frequency modulation techniques, the stimulation rate capabilities of any implantable visual prosthesis must be well above the CFF with an upper limit of the signal carrying capacity of individual optic nerve fibres which is of the order of 200 signals per second. In instances where large numbers of electrodes are employed, the stimulation rate is a linear multiple of the electrode quantity.

There exist several locations within the visual pathway that could conceivably be used for neurostimulation. Phosphenes have been elicited in the visual cortex [Brindley 1968], the geniculocalcarine tract [Marg 1965] and the superior colliculus [Nashold 1970]. Optic nerve stimulation has been shown to be a plausible site with successful recording of cortical responses obtained following stimulation [Shandurina 1986], and more recently, mapped phosphenes being conveyed in a human subject [Veraart 2003]. The correspondence of phosphenes with stimulation of retinal topography has demonstrated the plausibility of retinal stimulation [Humayun 1996].

The aforementioned represent potential intervention points for an artificial vision prosthesis. The direct brain stimulation approaches carry with them an inherent safety risk to the patient that arguably overshadows any potential benefit that could be acquired. Furthermore, it has been recognized since Brindley and Lewin's time that electrode quantities available in present technologies (limited to the order of tens of electrodes) are insufficient to convey useful vision at the visual cortex by virtue of the substantial area dedicated to vision within the brain and the disbursed phosphenes elicited by electrodes placed in close vicinity to one another in this region. Other areas of the brain do not lend themselves to sufficient degrees of access to justify attempts towards application of visual prostheses. Veraart's work [Veraart 2003] has shown the optic nerve to be an intervention site of substantial promise. Of particular difficulty, however, is the lack of corresponding mapping between phosphene percepts and electrode locations. This leads to the assertion that in the presence of viable neurons, the retina itself is the most efficacious site for a neural prosthesis for the restoration of vision and is the target of choice for the present proposed study. The CFF of the intact retina is dependent upon light intensity (Ferry-Porter Law). In an illustrative example of a television, no flicker is observed at a screen refresh rate of 25 Hz (interleaved wherein every second line of pixels is updated with each pass at 50 Hz) at moderate brightness. A different situation applies in electrical stimulation applied to the diseased retina. In these instances, intra-retinal processing is dysfunctional as a result of the disease, and what mechanisms that remain are by-passed by the way in which the bipolar and retinal ganglion cells are preferentially stimulated over other surviving neurons [Greenberg 1999][Rattay 2003]. The apparent result of this is a reduction in the duration of the perceived phosphenes.

In testing on human subjects, flicker fusion occurs at a two to three times the frequency in electrical stimulation when compared visual flicker fusion of normal eyes [Humayun 1999].

To avoid the perception of flicker, a single stimulation source must be capable of stimulating once every 20 ms. For pulse widths of the order of 1 ms each (2 ms with a charge recovery phase), as few as ten electrodes may be driven in series from a single source. For higher rates of stimulation, this problem is reduced to some extent but stimulation thresholds using constant current waveforms of durations substantially below 0.5 ms have not been reported.

To achieve and facilitate going beyond the frequency of stimulation necessary for even the most rudimentary conveyance of vision through a neural prosthesis, parallelization of stimulus is the only practical means of delivery. For this to be realized, a method is required to configure such a device such that instructions may arrive sufficiently quickly so as to allow for subsequent stimulation to occur without detectable delay.

Implantable neural prostheses require power and a means of configuration of the stimulus or stimuli they deliver. Power may be provided to the implant by way of an implanted battery, or other appropriate means including radio or inductive telemetry wherein signals transmitted by an external antenna are received and rectified so as to extract power. Configuration of the stimulus or stimuli to be delivered by an implantable neural prosthesis can be achieved by way of intrinsic means, that is, a pre-determined methodology such as the mechanisms present in sub-retinal neural prostheses including those of Chow et al. in U.S. Pat. No. 5,556,423 and others. In these devices, light incident upon the device evokes a specific outcome, based upon, for example, the intensity of said light in a particular region of the sub-retinal neural prosthesis. Configuration of the stimulus or stimuli to be delivered by an implantable neural prosthesis can be achieved by way of extrinsic means, that is, by instruction data delivered to said implantable neural prosthesis from an external source. The extrinsic method offers improved flexibility in configuring the implant and is used often in implantable neural prostheses including Crosby et al. U.S. Pat. No. 4,532,930 and Suaning U.S. Pat. No. 6,458,157. The present invention is primarily concerned with configuring an implantable neural prosthesis in an efficient way using the aforementioned extrinsic method of instructing said implant to perform functions pertaining to delivery of stimulus or stimuli.

Al Marshad et al. described a nerve prosthesis for pain inhibition that arranged electrodes in hexagonal configurations [AlMarshad 2001].

Scribner et al. described a retinal prosthesis with electrodes arranged in a hexagonal mosaic [Scribner 2001]. While not specifically described within the patent as utilizing a hexagonal mosaic of electrodes, Scribner's prosthesis is described in U.S. Pat. No. 6,393,327.

Both of the foregoing utilized electrodes arranged in a hexagonal mosaic, be it a single hexagon, or multiple clusters of hexagons comprising the entire electrode array. The present invention uses the hexagonal mosaic as a means by which efficient switching of electrodes to stimulating circuitry may be achieved.

PATENT REFERENCES

Chow et al. U.S. Pat. No. 5,556,423
Crosby et al. U.S. Pat. No. 4,532,930
Scribner U.S. Pat. No. 6,393,327
Suaning U.S. Pat. No. 6,458,157

NON-PATENT REFERENCES

Al Marshad, H. A., Lee, K. F., and Enderle, J. D. (2001) Induced Pain Inhibiting System (IPIS): New Technique to Manipulate Experimental Pain in Human Subject by Using Electrical Stimulation with Hexagonal Electrodes Ring Set. Proceedings of the IEEE 27th Annual Northeast Bioengineering Conference.
Brindley, G. S., Lewin, W. S. (1968). The sensations produced by electrical stimulation of the visual cortex. J Physiol (Lond), 196 (2):479 93.
Cha, K., Horch, K. and Normann, R. A. Simulation of a phosphene-based visual field: visual acuity in a pixelized vision system. Annals of Biomedical Engineering, 20: 439-449, 1992.
Greenberg, R. J., Velte, T. J., Humayun, M. S., Scarlatis, G. N. and de Juan, E. Jr. (1999). A computational model of electrical stimulation of the retinal ganglion cell. IEEE Trans. Biomed. Eng., 46: 505-514.
Huang, C Q, Carter, P M, Shepherd, R K, Seligman, P M, Tabor, B. Clark, G M. (1998) Direct Current Measurements in Cochlear Implants, An in-vivo and in-vitro Study. IEEE 2nd International Conference on Bioelectromagnetism, February Melbourne Australia.
Humayun, M. S., de Juan Jr., E., Dagnelie, G., Greenberg, R. J., Propst, R. H. and Phillips, D. H. (1996) Visual perception elicited by electrical stimulation of retina in blind humans. Arch Ophthalmol, 114 (1):40 6, 1996.
Humayun, M. S., de Juan Jr., E., Weiland, J. D., Dagnelie, G., Katona, S., Greenberg, R. J., and Suzuki, S. (1999) Pattern electrical stimulation of the human retina, Vis. Res., vol. 39, no. 15, pp. 2569-2576, July.
Marg, E. and Dierssen, G. (1965) Reported visual percepts from stimulation of the human brain with microelectrodes during therapeutic surgery. Confinia Neurologica, 26 (2): 57 75.
Nashold Jr., B. S. (1970) Phosphenes resulting from stimulation of the midbrain in man. Arch Ophthalmol, 84 (4):433 5.
Rattay, F., Resatz, S., Lutter, P., Minassian, K., Jilge, B. and Dimitrijevic, M. R. (2003). Mechanisms of electrical stimulation with neural prosthesis. Neuromodulation. 6: 42-56. Roth, B. (1995). The electrical properties of tissues. In: The Biomedical Engineering Handbook, Bronzino, J. D. (ed.), CRC Press, Florida. pp: 126-138.
Scribner, D., Humayun, M., Justus, B., Merritt, C., Klein, R., Howard, J. G., Peckerar, M., Perkins, F., Johnson, L., Bassett, W., Skeath, P., Margalit, E., Kah-Guan Au Eong, Weiland, J., de Juan, E., Finch, J., Graham, R., Trautfield, C., & Taylor, S. (2001). Intraocular retinal prosthesis test device. Proceedings of the 23rd Annual International Conference of the IEEE/Engineering in Medicine and Biology Society, 25-28 October, pp. 3430-3435.
Shandurina, A. N., and Lyskov, E. B. (1986). Evoked potentials to contact electrical stimulation of the optic nerves. Hum Physiol, 12 (1):9-16.
Veraart, C., Wanet-Defalque, M.-C., Grard, B., Vanlierde, A., and Delbeke, J. (2003) Pattern Recognition with the Optic Nerve Visual Prosthesis. Artificial Organs 27 (11), 996-1004.

BRIEF DESCRIPTION OF THE DRAWINGS

The invention will now be described in more detail, by way of example only, with reference to the accompanying drawings, in which.

Figure 1:
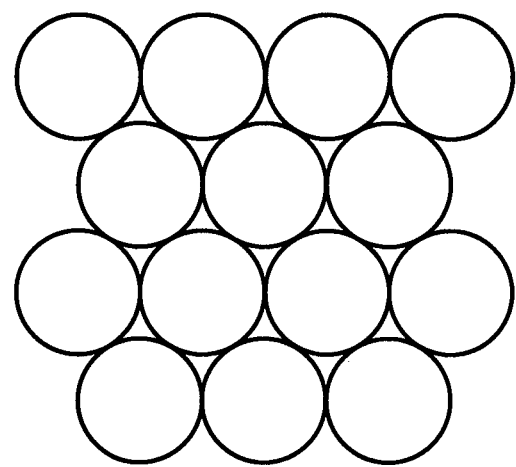
FIG. 1 is a plan view of 14 circles arranged in a staggered pattern to illustrate efficient packing of electrodes.

While the patent invention shall now be described with reference to the preferred embodiments shown in the drawings, it should be understood that the intention is not to limit the invention only to the particular embodiments shown but rather to cover all alterations, modifications and equivalent arrangements possible within the scope of appended claims.

Throughout this discussion which follows, it should be understood that the terms "implant", "neural prosthesis", "antenna", "radio signal", "radio telemetry", "data" and other terms of this nature are used in the functional sense and not exclusively with reference to specific medical devices, mechanical or electrical equivalents, components, or arrangements. Moreover, "array" includes one electrode, electrode-tissue interface or equivalent, or plurality of electrodes. Furthermore, "simultaneous stimulation" includes stimulation occurring in parallel both in part, or in whole as stimulation pulse widths need not be uniform.

DETAILED DESCRIPTION OF THE DRAWINGS

Prior Art

Figure 2:
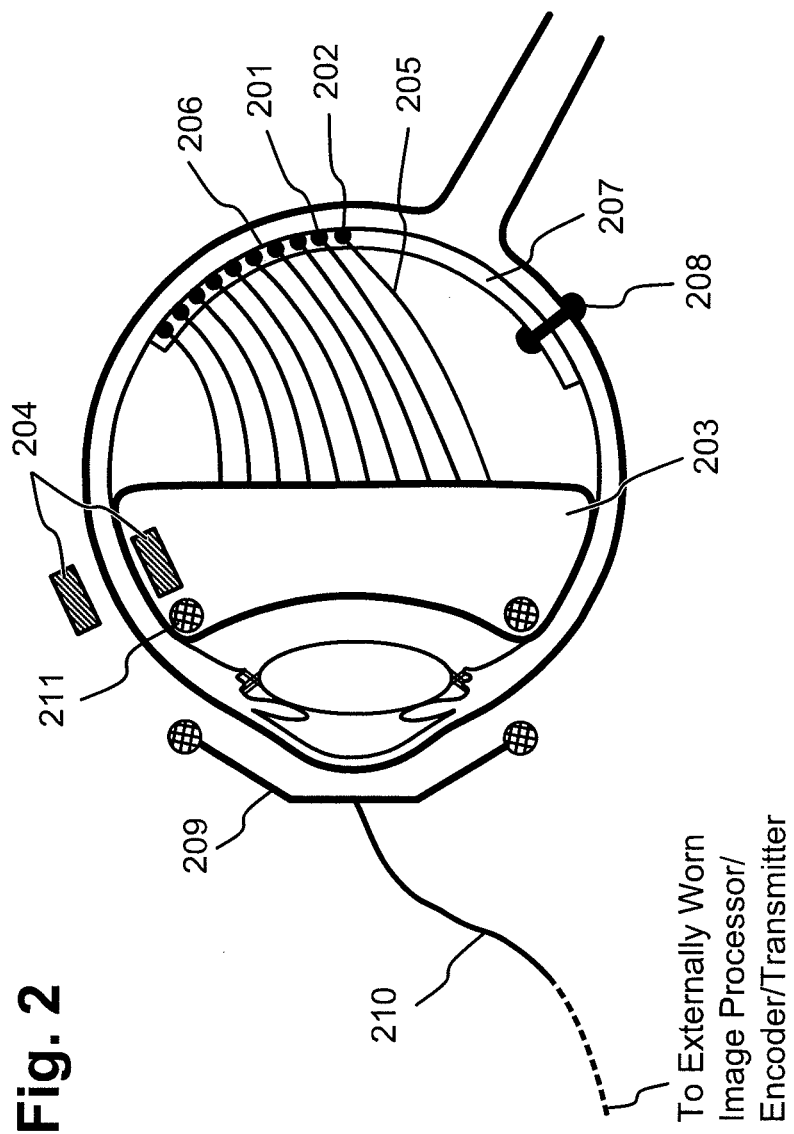
FIG. 2 is a cross-sectional view of an example neural prosthesis to illustrate the implementation of the present invention.

As an illustrative example, FIG. 2 shows a neural prosthesis implanted within the ocular anatomy. Transmitter cable 210 sends configuration data that is broadcast via radio signals from antenna 209, through the tissue of the eye and received by receiving antenna 211 within the eye. Said radio signals may be rectified for power, and decoded and checked for errors by the implant's electronics, housed within a hermetic capsule 203. Following decoding and error checking, electrical impulses or stimuli are passed through the hermetic capsule 203, along an interconnecting wire such as 205 and ending at the electrode-tissue interface 202. Electrical current injected into said electrode-tissue interface is returned to complete the electrical circuit by way of returning via any one or more of the electrode-tissue interfaces such as 201, or via a distant return electrode or electrodes (not shown) connected to the circuit within the hermetic capsule 203.

The present invention is primarily concerned with the minimization of the afore-described configuration data and the switching of current or voltage sources to the relevant electrodes involved in the neural stimulation described within said configuration data.

DESCRIPTION OF THE PREFERRED EMBODIMENT

The present invention is directed to a method for efficient multiplexing of a plurality of electrical signals to electrodes in a nerve stimulator using improved, predetermined, regular, repeatable geometric patterns arranged in a predetermined mosaic to form a desired array. While the array may be arranged upon the surface of virtually any geometric shape, according to one embodiment of the present invention, a contemplated array is projected upon a flat surface, such that the array pattern is of two dimensions. Multiple electrodes within said array are addressed by the nerve stimulator as being a stimulating electrode by an instruction specifying a single identifier, indicating a position within each regular geometric pattern. As such, each electrode within the array, maintaining the specified position within its respective repeatable geometric pattern, becomes a stimulating electrode and is connected to the appropriate electronic circuit for subsequent, potential use in nerve stimulation. In the illustrative example of the hexagon as the regular, repeatable geometric pattern, said multiplexing achieves addressing of stimulating electrodes that does not limit the quantity of electrodes within said array. Furthermore, in said illustrative example, no stimulating electrode specified by the single identifier is immediately adjacent to any other stimulating electrode specified by the same identifier. Moreover, all electrodes can be separated by the same linear distance.

To complete an electrical circuit through the conducting or non-conducting media within which the array is placed, a return electrode or electrodes may be specified. These may be addressed as a single return electrode either within or outside of the array, or, by implementing a similar addressing method to that described above, any one or all non-stimulating electrodes within each regular geometric pattern may be specified as being the return electrode or electrodes. By adding an additional boolean instruction to the multiplexing circuit, adjacent pairs of electrodes within each regular geometric pattern may be used as return electrodes. Further instructions can facilitate more complicated combinations of return electrodes within any regular geometric pattern. In the case of using all non-stimulating electrodes within each regular geometric pattern, a so called "guard ring" is formed, that reduces the transfer of charge to or from adjacent and distant stimulating electrodes and their respective return electrodes. At the periphery of an array, partial guard rings are formed as a result of guard ring formation.

This connection between the packing problem and that of an electrode array for a visual prosthesis has heretofore eluded all researchers working in this field who have proposed rectangular, staggered or other non-hexagonal patterns for their electrode configurations.

Therefore, according to the present invention, a novel and versatile multiplexing method may be derived such that a small amount of information serves to configure the stimulus delivery to an electrode array of unlimited dimensions.

Figure 3:
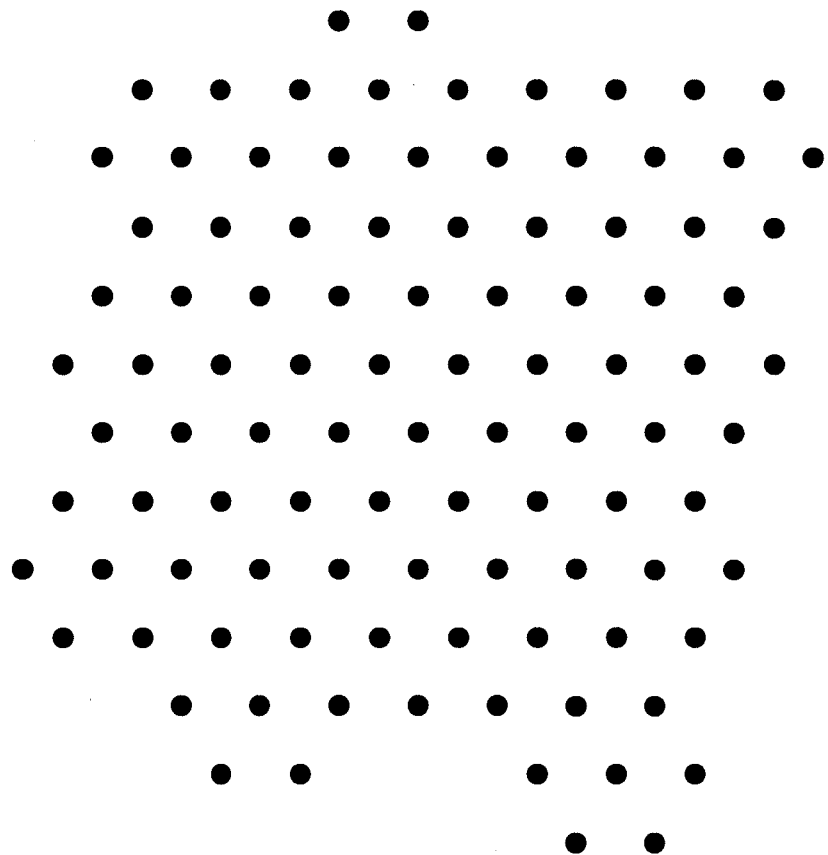
FIG. 3 is a plan view of an example electrode array layout with electrodes arranged in a hexagonal mosaic.

As an illustrative example, FIG. 3 shows a layout of an electrode array comprising 98 electrodes. The principal advantage of the hexagon arrangement of electrodes is the means by which individual electrodes may be addressed in parallel to facilitate parallel stimulation. Consider the hexagon shapes shown in FIG. 4 which are overlaid upon the electrode geometry of FIG. 3. Each of the 14 hexagons shown contains seven electrodes (98 electrodes in total). These hexagons form the "base hexagon shapes" that will be referred to in subsequent discussion. One may assign one current or voltage source (source) to each hexagon.

Figure 4:
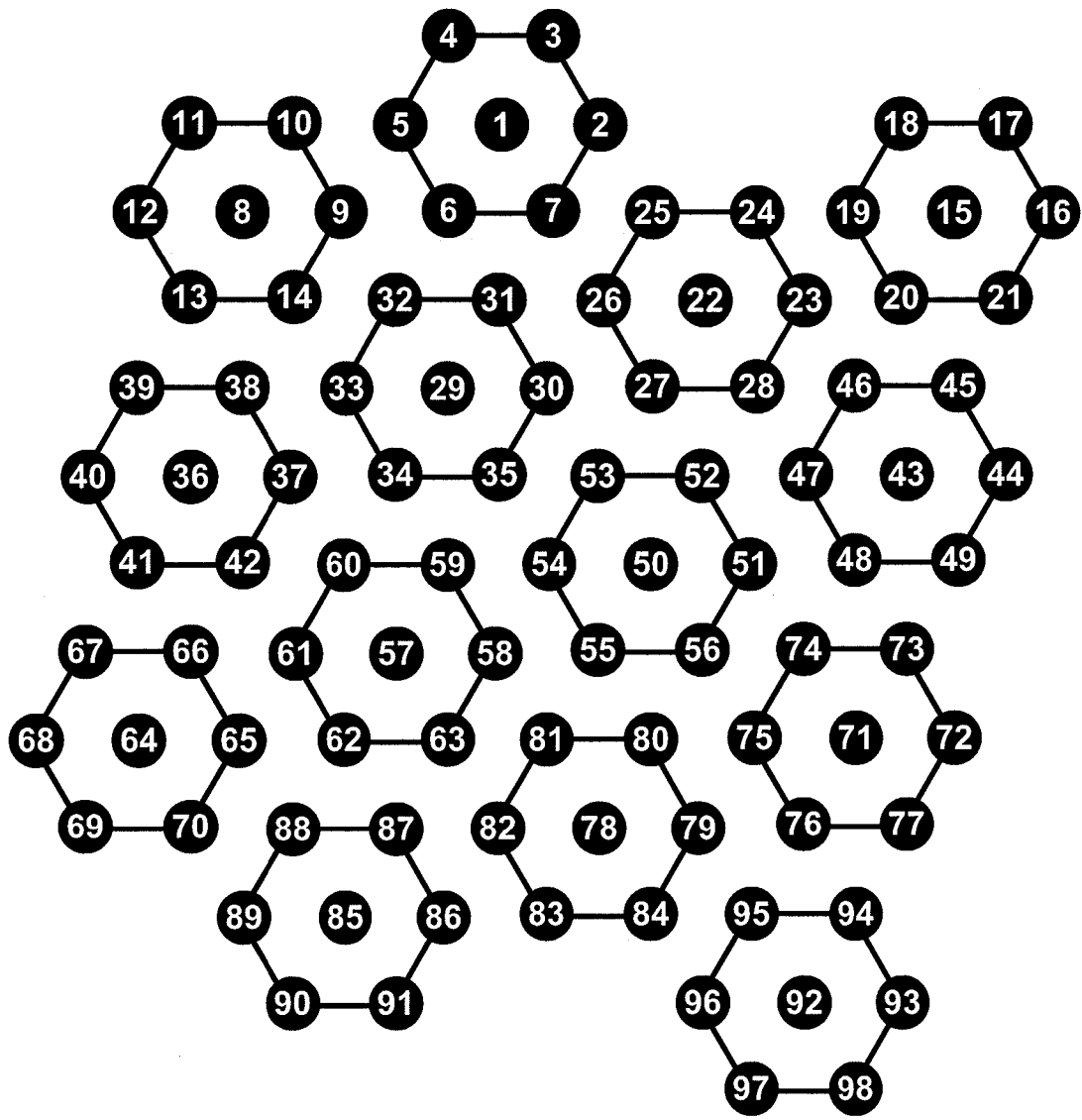
FIG. 4 is a repeat of FIG. 3 with hexagons superimposed upon each subset of the hexagonal mosaic.
Figure 5:
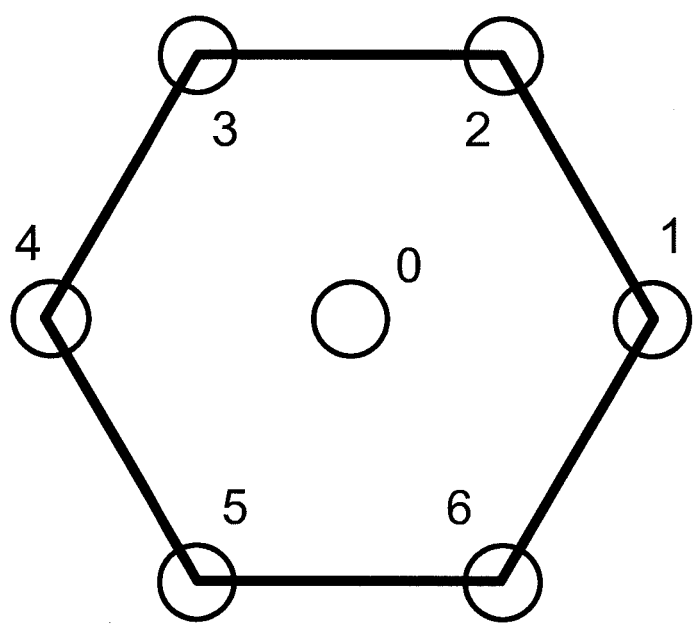
FIG. 5 shows an example numbering scheme for electrode positions within a hexagon.
Figure 6:
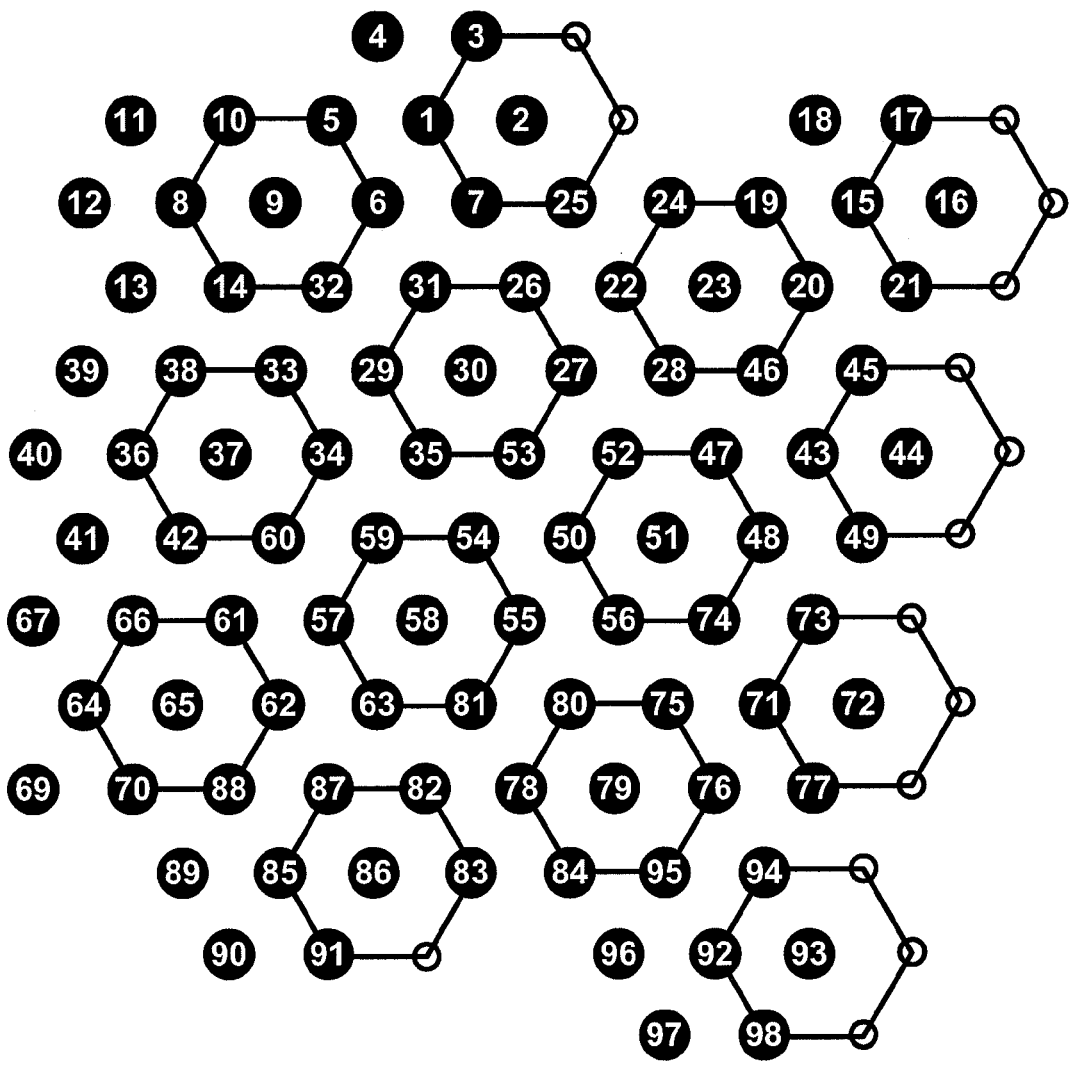
FIG. 6 shows a variant of FIG. 4 with superimposed hexagons shifted by one position.
Figure 7:
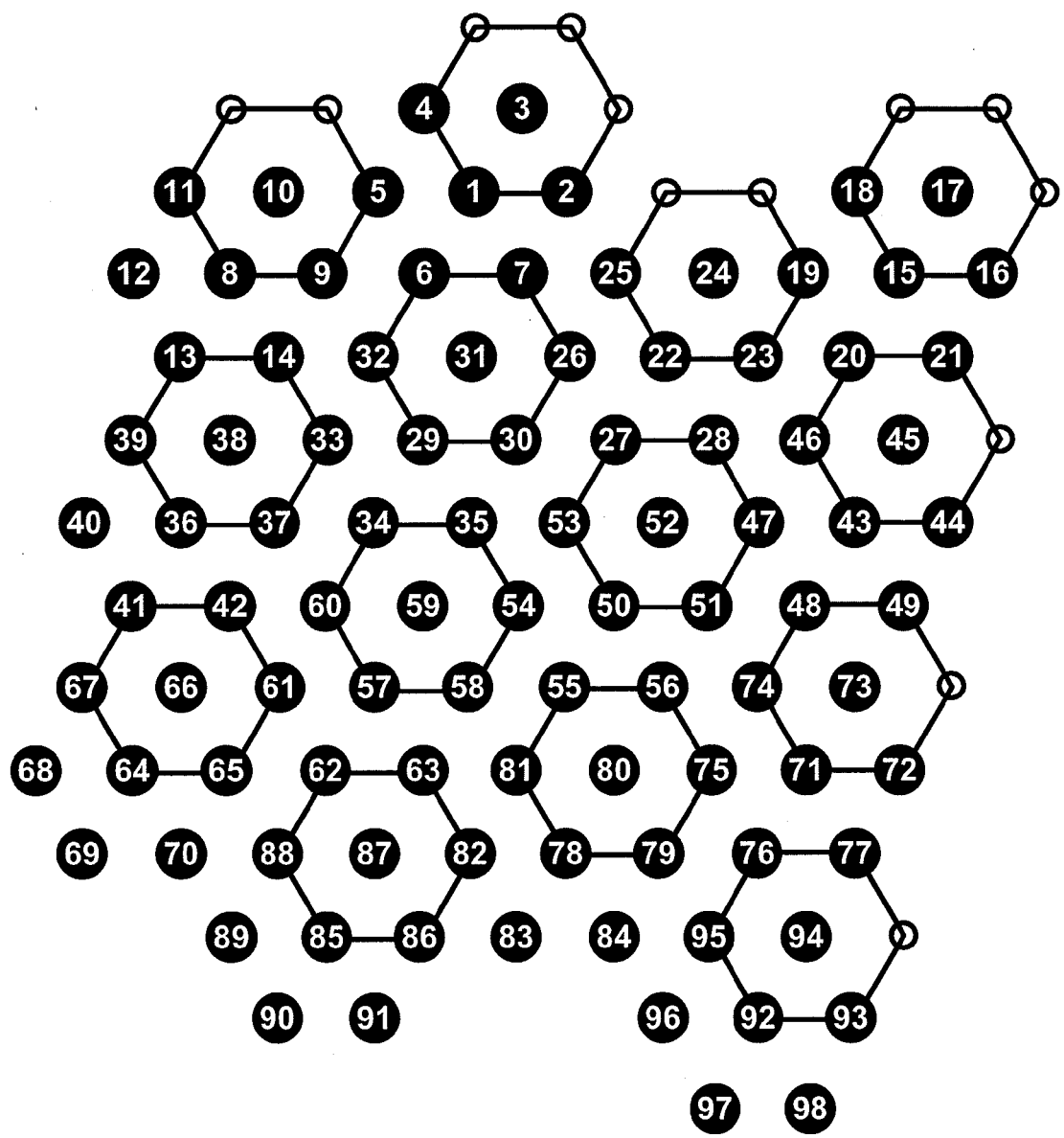
FIG. 7 shows a variant of FIG. 4 with superimposed hexagons shifted by two positions.
Figure 8:
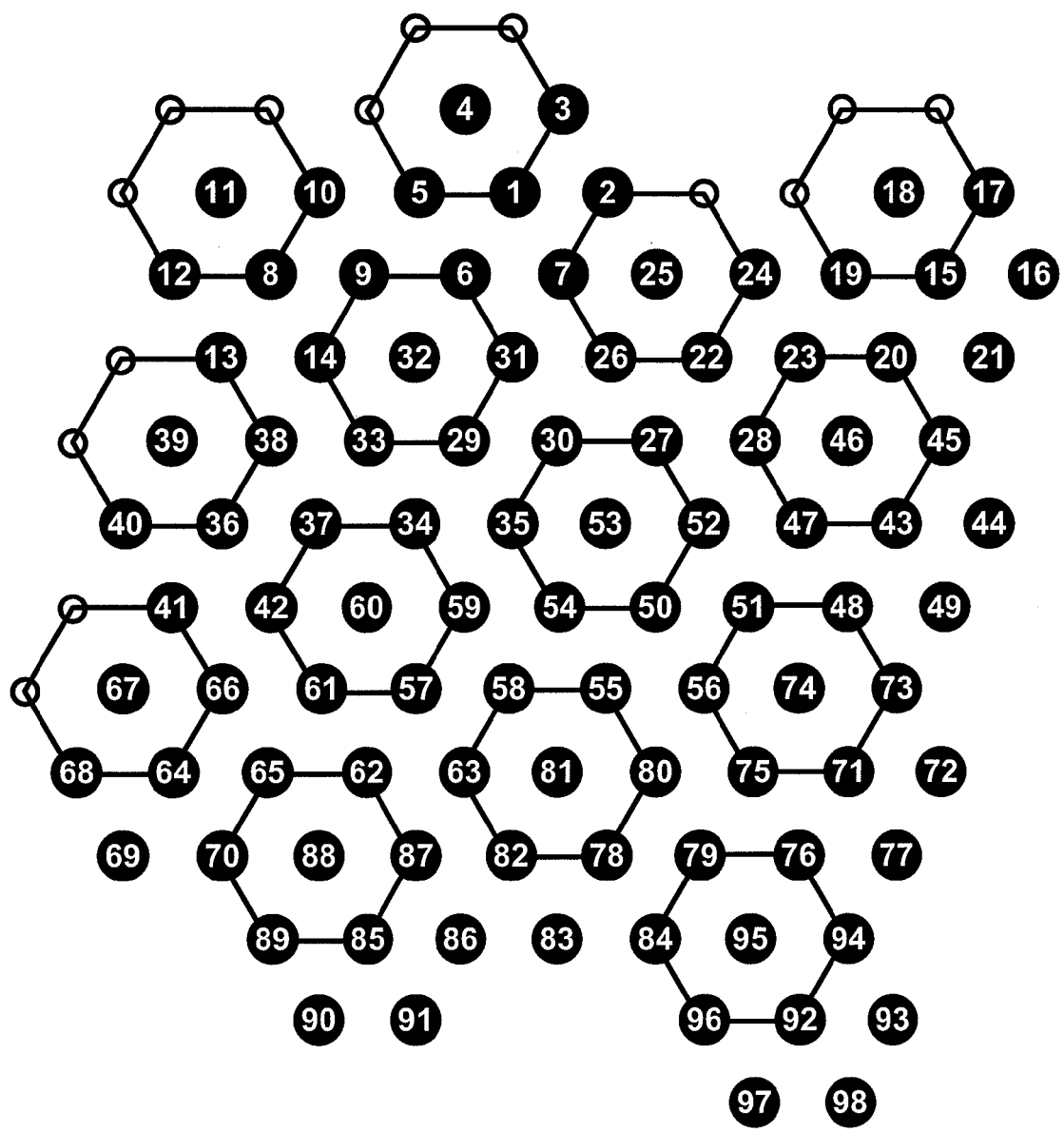
FIG. 8 shows a variant of FIG. 4 with superimposed hexagons shifted by three positions.
Figure 9:
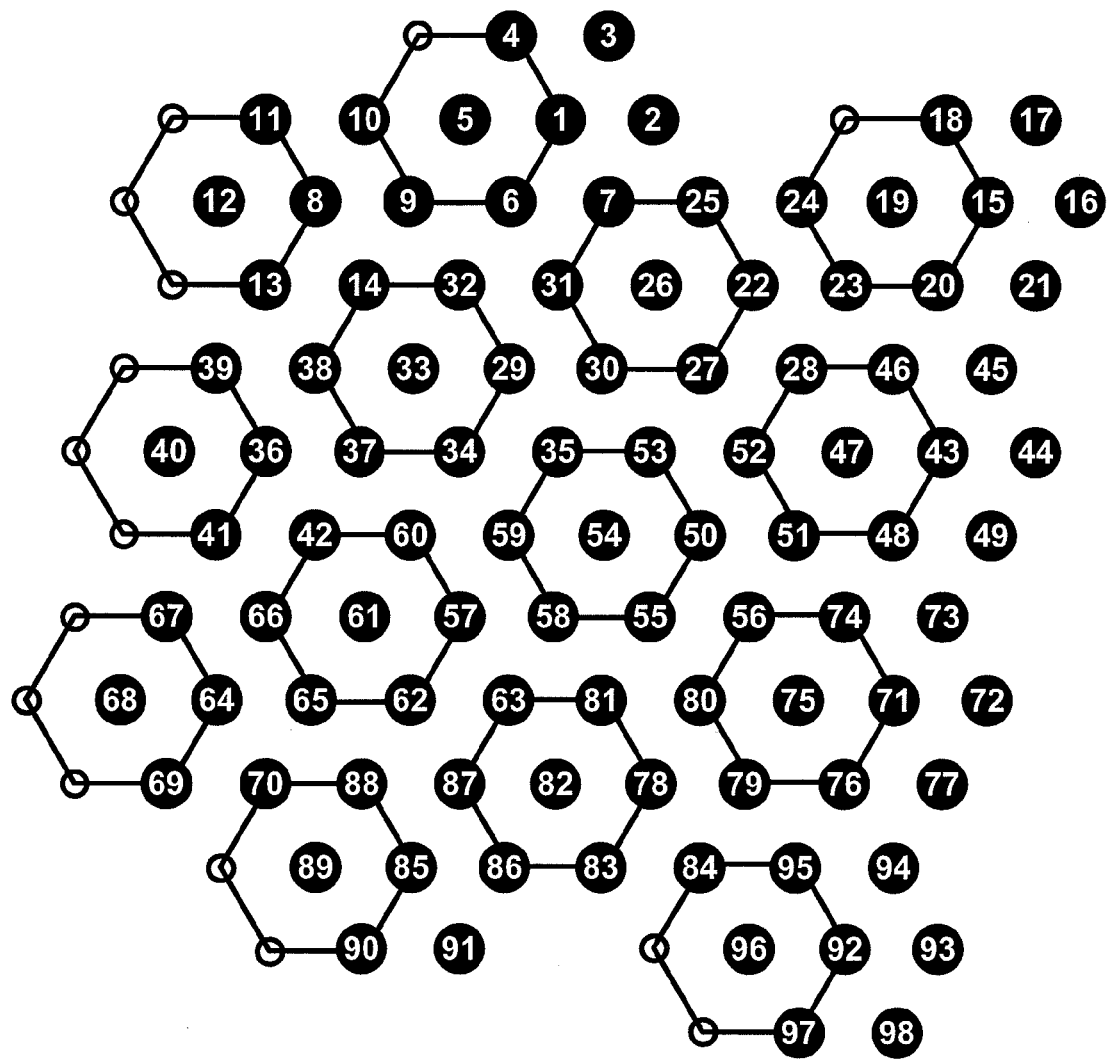
FIG. 9 shows a variant of FIG. 4 with superimposed hexagons shifted by four positions.
Figure 10:
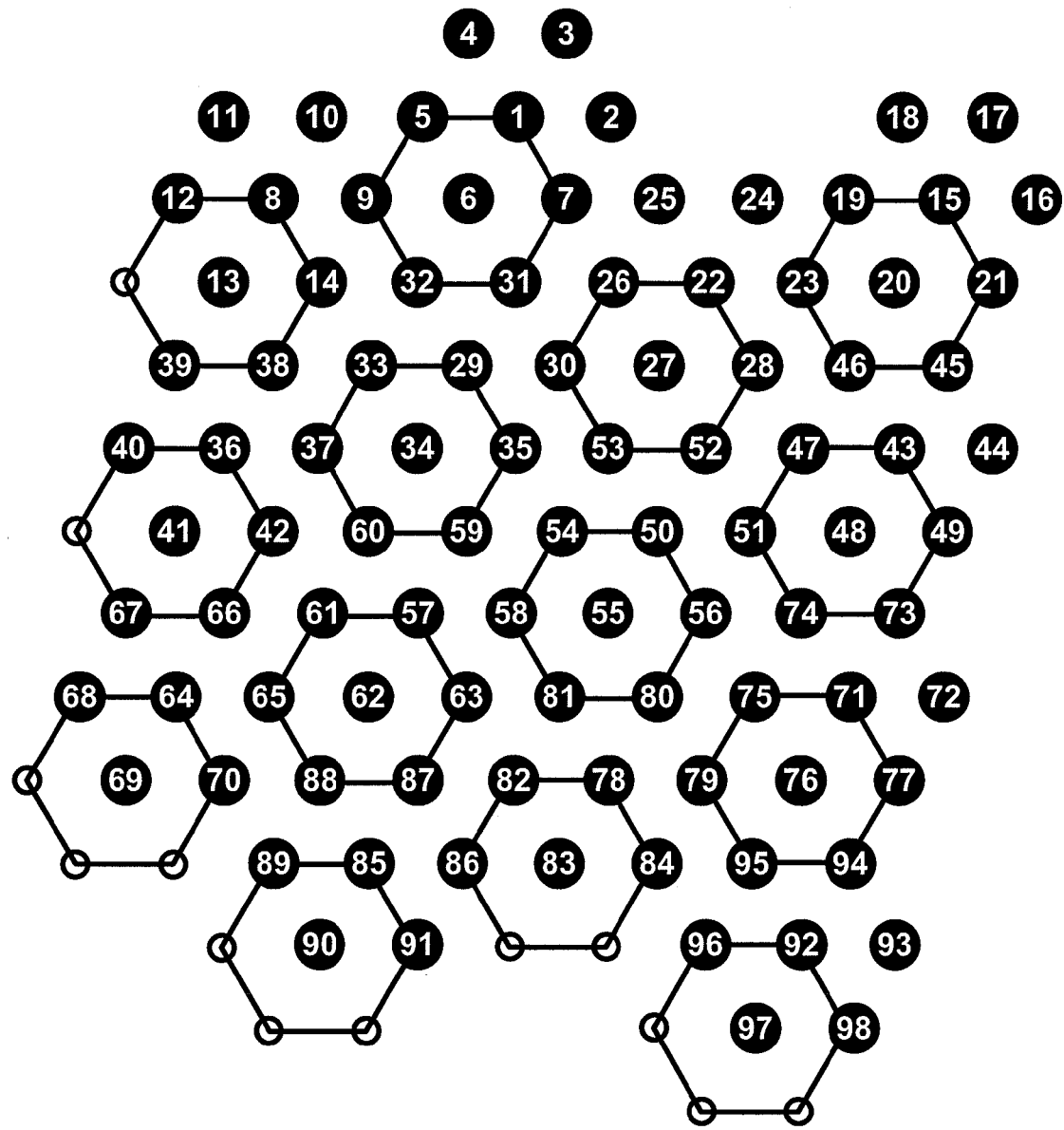
FIG. 10 shows a variant of FIG. 4 with superimposed hexagons shifted by five positions.
Figure 11:
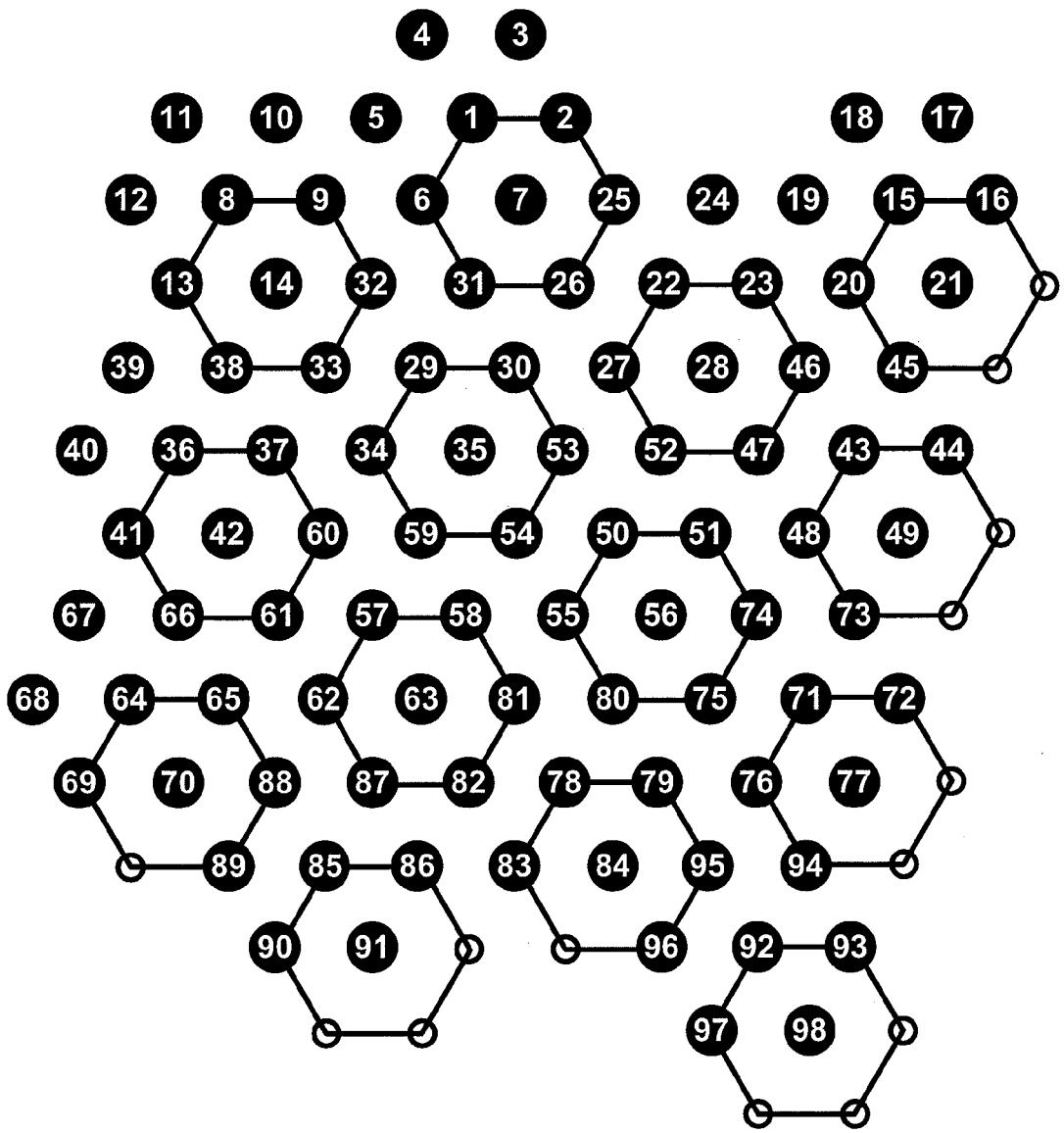
FIG. 11 shows a variant of FIG. 4 with superimposed hexagons shifted by six positions.

By specifying a position using, for example, the numbering scheme of FIG. 5 (or another appropriate identifying scheme), one may specify the center electrode of a hexagon pattern which may be superimposed upon the electrode layout shown in FIG. 3. In addition to FIG. 4, FIGS. 6 through 12 illustrate seven different patterns that may be generated by specifying a single number (0-6) denoting the center of the hexagon. Note that all hexagons are configured throughout the array by specifying a single number (0-6) as illustrated in FIG. 5 (see uppermost hexagon of FIGS. 4, and 6 through 12) such that the center of each hexagon is separated from the centers of its adjacent hexagon neighbors by equal distances throughout the array. An electrode array of such hexagonal layout may possess infinite dimensions and remain addressable in this fashion.

In basic operation, the center of each base hexagon shape serves as the stimulating electrode. One two, or all of the immediately adjacent electrodes (those electrodes at the corners of the hexagon shapes) or a distant monopolar return-path electrode serves as the electrical return path for stimulus. During the first phase of biphasic stimulus, the center electrode in the hexagon is connected to the source associated with its respective hexagon. Return path electrodes are connected to either a supply voltage or to a current or voltage sink (sink). During the second (charge recovery) phase of biphasic stimulation, the opposite is true.

For the stimulating electronics and the electrode array to possess the necessary versatility for a wide range of stimulation paradigms, it is necessary to maintain the ability for any electrode within the array to be capable of being the stimulating electrode. Re-positioning the hexagon orientations to six "new" positions as shown in FIGS. 6 through 11, the placement of any electrode at the center of a hexagon shape is illustrated, thus enabling stimulus to occur from any electrode in the same fashion to that described in the foregoing text. Put another way, there exist seven different ways to orient equidistant hex shapes on the array.

Figure 12:
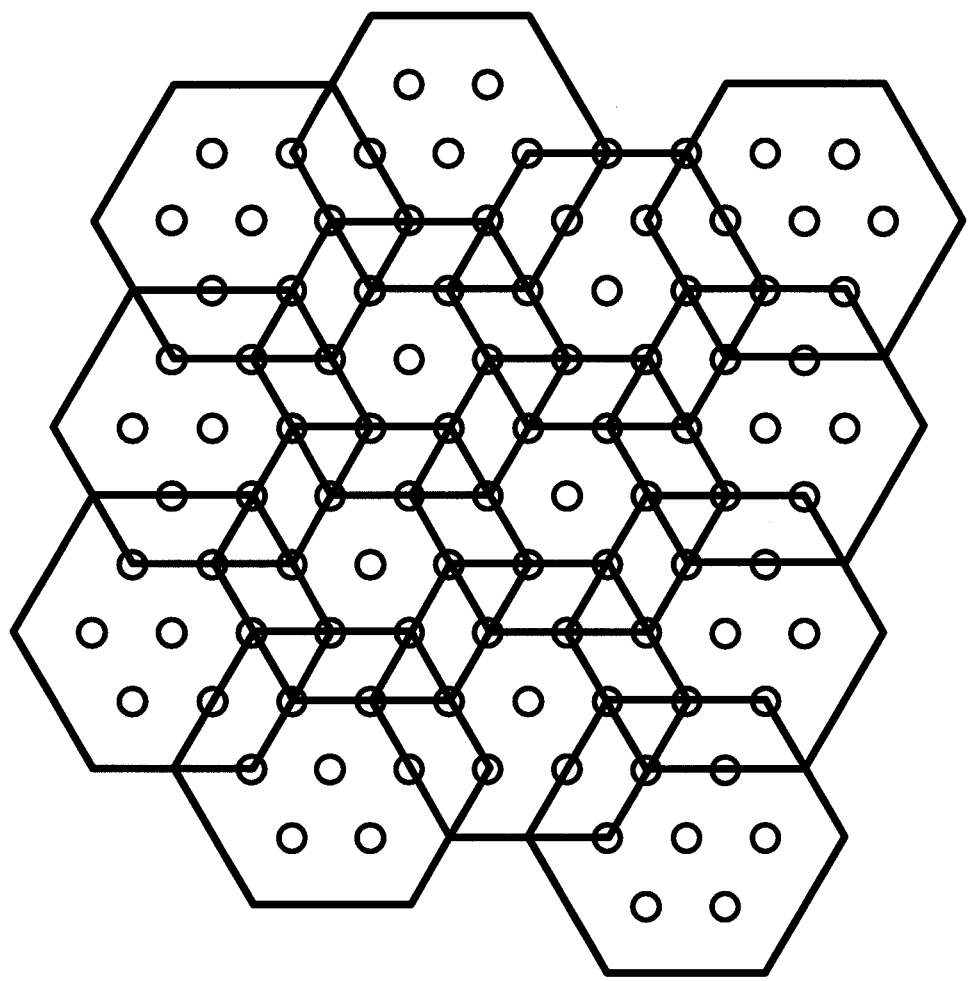
FIG. 12 is a plan view of the example electrode array of FIG. 3 illustrating the sharing of current or voltage sources across the hexagons that comprise the hexagonal mosaic.

Note carefully that deviations from the base hexagon shapes illustrated in FIG. 4 require some electrodes from adjacent base hexagon shapes to become included into the re-oriented shapes. This, in effect, requires that some electrodes from adjacent base hexagon shapes possess the ability to be connected to the source associated with adjacent base hexagon shapes. Thus, each source has a "region of influence" outside its base hexagon shape. The "regions of influence" overlap in several locations as illustrated in FIG. 12.

An electrode may be connected to one of as many as three sources such that the electrode may participate in stimulation originating from any of its immediately adjacent neighbours. Note that owing to edge effects, not all electrodes require connections to three sources.

Enhancements

While the present invention primarily pertains to implementations of retinal neuroprostheses, advantage is realized by utilizing the same addressing technique in other areas of neuroprosthesis wherein two-dimensional electrode arrays or indeed electrode arrays that may be approximated by a two-dimensional array such as electrodes for the auditory brainstem.

Figure 13:
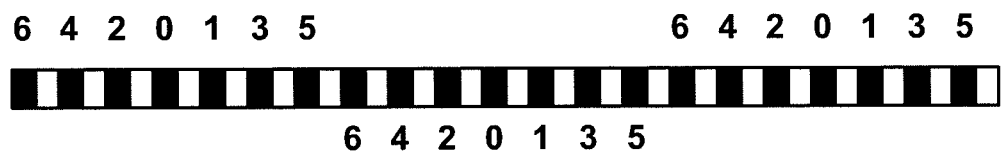
FIG. 13 is a plan view of an example cochlear implant electrode array with shaded regions indicating electrodes.

Further advantage can be realized in other regular, repeatable geometric patterns other than the hexagon layout. For example, in the case of cochlear implants for the deaf or hearing impaired, electrodes are typically arranged in a linear pattern so as to provide a means of insertion within the cochlea while at the same time maintaining advantage of the tonotopic mapping of the cochlea. An abstraction of the hexagon into a linear arrangement, with the central electrode of the hexagon arranged centrally adjacent to the surrounding electrodes (see FIG. 13) can provide an efficient means of multiplexing using the same addressing methodology. For example, in reference to FIG. 13, consider a linear electrode comprised of 21 electrodes, grouped in three sets of seven electrodes each. In this abstraction of the hexagon multiplexing method, as many as three electrodes may be stimulated simultaneously. The return path for each stimulating electrode may be the immediately adjacent electrode(s), electrode(s) adjacent plus one position, adjacent plus two positions, or all of these. Similar abstraction of this arrangement can be applied to neural cuff electrodes.

Using the self similarity of scale in the electrode arrangement, clusters comprised of subunits formed by repeatable geometric patterns with each electrode within each said repeatable geometric pattern connected together electrically, larger areas of stimulation may be achieved by considering said clusters each as individual single entities. For example, all seven electrodes comprising a hexagon may be connected together electrically to effectively form a single electrode, albeit spread across seven locations. Thence the same multiplexing scheme may be applied to this entity and its surrounding entities at a larger scale.

The foregoing does not limit the possibility of applying two current or voltage sources to each hexagon, one for emitting electrical current, the other for collecting electrical current. While increasing the complexity of the switching logic, the overall methodology of switching remains.

Benefits of the Invention

The data necessary to configure an implantable neural prosthesis must be received and be acted upon sufficiently quickly in order for the stimulus to be delivered efficaciously. In other words, the configuration of the stimuli should not be the rate-limiting factor in the delivery said stimuli. Configuring an implant for delivering an event of electrical stimulation usually requires at least the following information:

instruction of the electrode or electrodes to be used in the delivery of electrical current to neural tissue; instruction of the electrode or electrodes to be used to return in the return of electrical current from said neural tissue; instruction of the magnitude of the stimulus to be delivered; instruction of the duration of the stimulus to be delivered.

The present invention describes a method of providing and acting upon the foregoing information in an efficient manner that is not limited by the quantity of electrodes present as part of the neural prosthesis. The present invention facilitates singular or simultaneous stimulations in complex combinations by configuring the entire event of electrical stimulation with a small quantity of data.

Other Embodiments

From the foregoing description, it will thus be evident that the present invention provides a method for multiplexing electrodes in a neural prosthesis. As various changes can be made in the above embodiments and operating methods without departing from the spirit or scope of the following claims, it is intended that all matter contained in the above description or shown in the accompanying drawings should be interpreted as illustrative and not in a limiting sense.

Variations or modifications to the design and construction of this invention, within the scope of the appended claims, may occur to those skilled in the art upon reviewing the disclosure herein. Such variations or modifications, if within the spirit of this invention, are intended to be encompassed within the scope of any claims to patent protection issuing upon this invention.

The invention claimed is:

1. A multiplexing method for a neural prosthesis comprising a plurality of electrodes, the method comprising:
generating a mosaic of regular, repeatable geometric patterns and superimposing said mosaic on the plurality of electrodes, each regular, repeatable geometric pattern being associated with at least two of the plurality of electrodes associated therewith;
specifying a stimulating electrode within each of said regular, repeatable geometric patterns using a single stimulation identifier;
associating all stimulating electrodes specified by the single stimulation identifier with a power source; and
specifying an electrical return path for each stimulating electrode.

2. The method of claim 1, wherein each stimulating electrode is automatically associated with one of a current source and a voltage source.

3. The method of claim 2, wherein a plurality of said stimulating electrodes are controllable to deliver electrical stimulus simultaneously.

4. The method according to claim 1, wherein the single stimulation identifier corresponds to a particular position within said regular, repeatable geometric patterns.

5. The method according to claim 1, wherein the mosaic is generated such that each stimulating electrode specified by the single stimulating identifier is associated with a plurality of non-stimulating electrodes, the non-stimulating electrodes forming a guard such that charge transfer between the stimulating electrodes of the regular, repeatable geometric patterns is reduced.

6. The method according to claim 5, wherein the guard surrounding at least one stimulating electrode is a partial guard which partially surrounds the stimulating electrode.

7. The method of claim 1, wherein the mosaic is treated as a single entity and used as a subunit to form a larger mosaic of regular, repeatable geometric patterns.

8. The method according to claim 5, wherein the guard surrounding at least one stimulating electrode is a ring of non-stimulating electrodes which surrounds the stimulating electrode.

9. The method of claim 1, wherein the stimulating electrode within each regular, repeatable geometric pattern is individually controllable to deliver electrical stimulus.

10. The method of claim 1, further comprising:
associating each regular, repeatable geometric pattern with a power source; and wherein
the step of associating all stimulating electrodes specified by the single stimulation identifier to a power source includes associating each stimulating electrode to the power source associated with the regular, repeatable geometric pattern which the stimulating electrode is part of.

11. The method of claim 4, wherein the single stimulation identifier corresponds to a central position within said regular, repeatable geometric patterns.

12. The method of claim 1, wherein specifying an electrical return path for each stimulating electrode comprises:
specifying at least one electrical return path electrode within each of said regular, repeatable geometric patterns by using a single return path identifier; and
associating each return path electrode specified by the single return path identifier to a sink that in use draws current via the electrical return path.

13. The method of claim 12, further comprising
associating each regular, repeatable geometric pattern with one of a supply voltage, a current sink, and a voltage sink, and wherein
associating each return path electrode specified by the single return path identifier to a sink comprises associating each return path electrode to the sink associated with the regular, repeatable geometric pattern which the return path electrode is part of.

14. The method of claim 12, wherein the single return path identifier specifies a single return path electrode within each of said regular, repeatable geometric patterns.

15. The method of claim 14, wherein the single return path electrode within each of said regular, repeatable geometric patterns is positioned at a periphery of the geometric pattern.

16. The method of claim 12, wherein the single return path identifier specifies a plurality of return path electrodes within each of said regular, repeatable geometric patterns.

17. The method of claim 16, wherein the plurality of return path electrodes within each of said regular, repeatable geometric patterns are positioned at a periphery of the geometric pattern.

18. The method of claim 1, wherein specifying an electrical return path for each stimulating electrode comprises:
specifying a common monopolar return path, the common monopolar return path being common to a plurality of stimulating electrodes.

19. The method of claim 18, wherein the common monopolar return path is common to all stimulating electrodes.

20. The method of claim 12, further comprising:
using a single grouping identifier to specify that the electrical return path electrode within each regular, repeatable geometric pattern as specified by the single return path identifier is grouped with one or more other return path electrodes in the same regular repeatable pattern.

21. The method of claim 20, wherein the single grouping identifier specifies that the return path electrode in each regular repeatable pattern as specified by the single return path identifier is grouped with one or more adjacent electrodes in the same regular repeatable pattern.

22. The method of claim 20, wherein the single grouping identifier specifies that the return path electrode in each regular repeatable pattern as specified by the single return path identifier is grouped with one or more non-adjacent electrodes in the same regular repeatable pattern.

23. The method of claim 20, wherein the single grouping identifier specifies that the return path electrode in each regular repeatable pattern as specified by the single return path identifier is grouped with all other non-stimulating electrodes in the same regular repeatable pattern.

24. The method of claim 1, wherein each stimulating electrode specified by the single stimulation identifier is connected to a different power source.

25. The method of claim 1, wherein the single stimulation identifier specifies a plurality of stimulating electrodes within each of said regular, repeatable geometric patterns.

26. The method of claim 1, wherein the electrodes are configured to stimulate one or more retinal neurons of a recipient.

27. The method of claim 1, wherein the electrodes are configured to stimulate one or more cochlea neurons of a recipient.

28. The method of claim 1, wherein the single stimulation identifier is an integer number.

29. The method of claim 10, wherein the single return path identifier is an integer number.

30. The method of claim 17, wherein the single grouping identifier is a Boolean value.

31. The method of claim 1, wherein said regular, repeatable geometric patterns are hexagonal patterns.

32. The method of claim 1, wherein said regular, repeatable geometric patterns are linear patterns.

33. The method of claim 1, wherein the single stimulation identifier specifies stimulating electrodes in each regular, repeatable geometric pattern such that each stimulating electrode is separated from all other stimulating electrodes by at least one non-stimulating electrode.

34. A neural prosthesis comprising:
a plurality of electrodes; and
a multiplexer for multiplexing a plurality of signals to said plurality of electrodes, the multiplexer configured to perform the method of claim 1.

35. The neural prosthesis of claim 34, wherein a plurality of said stimulating electrodes are controllable to deliver electrical stimulus simultaneously.

36. The neural prosthesis of claim 34, wherein each stimulating electrode within each regular, repeatable geometric pattern is individually controllable to deliver electrical stimulus.

37. The neural prosthesis of claim 34, wherein to specify an electrical return path for each stimulating electrode the multiplexer is further configured to:
specify at least one electrical return path electrode within each of said regular, repeatable geometric patterns by using a single return path identifier; and
associate each return path electrode specified by the single return path identifier to a sink that in use draws current via the electrical return path.

38. The neural prosthesis of claim 37, wherein the multiplexer is further configured to:

associate each regular, repeatable geometric pattern with one of a supply voltage, a current sink, and a voltage sink, and wherein the association of each return path electrode specified by the single return path identifier to a sink or voltage sink comprises associating each return path electrode to the sink associated with the regular, repeatable geometric pattern which the return path electrode is part of.

39. The neural prosthesis of claim 37, wherein the single return path identifier specifies a single return path electrode within each of said regular, repeatable geometric patterns.

40. The neural prosthesis of claim 37, wherein the single return path identifier specifies a plurality of return path electrodes within each of said regular, repeatable geometric patterns.

41. The neural prosthesis of claim 37, wherein the multiplexer is further configured to:

use a single grouping identifier to specify that the electrical return path electrode within each regular, repeatable geometric pattern as specified by the single return path identifier is grouped with one or more other return path electrodes in the same regular repeatable pattern.

42. The neural prosthesis of claim 34, wherein the plurality of electrodes are configured to stimulate one or more retinal neurons of a recipient.

43. The neural prosthesis of claim 34, wherein the plurality of electrodes are configured to stimulate one or more cochlea neurons of a recipient.

\* \* \* \* \*